United States Patent [19]

Pera et al.

[11] 4,285,765

[45] Aug. 25, 1981

[54] SLIME CONTROL COMPOSITIONS AND METHODS OF USING THE SAME

[75] Inventors: John D. Pera; Betty S. Johnson, both of Memphis, Tenn.

[73] Assignee: Buckman Laboratories, Inc., Memphis, Tenn.

[21] Appl. No.: 190,125

[22] Filed: Sep. 24, 1980

[51] Int. Cl.³ .............................................. D21H 3/02
[52] U.S. Cl. .................................. 162/161; 162/190; 71/67; 210/764; 424/270; 71/67;90;105
[58] Field of Search ................ 162/161, 190; 210/764; 424/270

[56] References Cited

U.S. PATENT DOCUMENTS

| | | | |
|---|---|---|---|
| 3,231,509 | 1/1966 | Shema | 71/103 |
| 3,520,976 | 7/1970 | Buellman et al. | 162/161 |
| 3,929,562 | 12/1975 | Shema et al. | 162/161 |
| 3,930,015 | 12/1975 | Swored et al. | 162/161 |

*Primary Examiner*—William F. Smith
*Attorney, Agent, or Firm*—Floyd Trimble

[57] ABSTRACT

The present invention relates to certain compositions and processes useful for inhibiting the growth of microorganisms in water and, in particular, water used for industrial purposes; for example, in the manufacture of paper, in cooling water systems, in effluent water treatment, and in secondary recovery petroleum operations. The novel processes and compositions of the present invention are processes or mixtures which show unexpected synergistic activity against microorganisms, including bacteria, sulfate-reducing bacteria, fungi, and algae, which produce slime in aqueous systems where such slime is objectionable from either an operational or aesthetic point of view. Specifically, the invention is directed to the use of compositions comprising 2-(thiocyanomethylthio)benzothiazole and 2,2-dibromo-3-nitrilopropionamide.

8 Claims, No Drawings

SLIME CONTROL COMPOSITIONS AND METHODS OF USING THE SAME

BACKGROUND OF THE INVENTION

Many industrial products when wet or when subjected to treatment in water are normally susceptible to bacterial and/or fungal degradation or deterioration if means are not taken to inhibit such degradation or deterioration. Wood pulp, wood chips, starch and proteinaceous substances, animal hides, vegetable tanning liquors, and leather are all damaged or degraded by growth of bacteria and other microorganisms or by enzymes produced by such growth. Wet pulp containing about 25 percent moisture content is subject to attack by stain, mold, and decay fungi. If not controlled, the result is a loss of useful fiber in badly decayed pulp, difficulty in dispersing partially decayed pulp, a darkening in color, and the development of undesirable odors caused by the growth of the microorganisms. Different species of molds are encountered at various stages in the manufacture of leather. As an example, soaking provides an environment highly conductive to the growth of microorganisms, and even strong pickle solutions are subject to attack by some microorganisms. Molds in particular may be troublesome and cause discoloration of the pickled stock, especially if it is held for a period of time. During the chrome tanning process, the chrome tanned stock held "in the blue" readily molds and is discolored. Mold growth may develop on heavy vegetable tanned leather during the drying period and produce spots and stains on either the flesh or grain sides.

Another objectionable phenomenon occurring in industrial process systems involving water is slime formation. Slime consists of matted deposits of microorganisms, fibers, and debris, and it may be stringy, pasty, rubbery, tapioca-like, hard, or horny, and it may have a characteristic odor that is different from that of the liquid suspensions in which it is formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeasts, and yeast-like organisms.

Besides being objectionable from the standpoint of general cleanliness and sanitation in breweries, wineries, dairies, paper mills, and other industrial plants or establishments, slime may interfere and produce plugging of screens in pulp and paper systems, thus reducing their efficiency. When large amounts of slime become incorporated in the paper sheet, its strength is reduced, and it may consequently break and require rethreading of the machine. In the paper itself, slime may be responsible for unsightly spots, holes, and odors and may produce general discoloration throughout the sheet.

Sulfate-reducing bacteria are generally present in waters used for the secondary recovery of petroleum. The presence of these bacteria is objectionable if not controlled. For example, these organisms are able to reduce sulfates present in the injection water to sulfides which in turn react with soluble iron salts to form insoluble iron sulfide. As a result, matted deposits are produced consisting of sulfides, occluded oil, plus any other solids that may be present. This is undesirable because water containing such deposits when injected into subterranean formations causes the plugging thereof. Furthermore, sulfate-reducing bacteria cause corrosion of metal by accelerating galvanic action. Microbiological corrosion is well recognized and is a major economic problem in the petroleum industry.

It is, therefore, a principal object of the present invention to provide a synergistic composition for the control of microorganisms that are responsible for the formation of slime in aqueous systems.

It is another object of this invention to provide an improved process for controlling slime-forming microorganisms in aqueous systems such as pulp and paper mill systems, cooling water systems, and secondary recovery petroleum operations.

These and other objects and advantages of the novel compositions and processes of this invention will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

In brief, the foregoing objects and advantages are obtained by utilizing compositions comprising synergistic mixtures of 2-(thiocyanomethylthio)benzothiazole and 2,2-dibromo-3-nitrilopropionamide.

The compositions of this invention are utilized for controlling the growth and reproduction of slime-forming microorganisms by adding the compositions to cooling water systems, pulp and paper mill systems, pools, ponds, lagoons, lakes, etc., in an amount sufficient to control the slime-forming microorganisms which are present in the system which is treated.

The organic microbicides comprising the compositions of this invention are commercially available compounds or easily synthesized from commercially available raw materials. The preparation of 2-(thiocyanomethylthio)benzothizaole is described in U.S. Pat. No. 3,520,976. The 2,2-dibromo-3-nitrilopropionamide is a commercially available microbicide manufactured by the Dow Chemical Company of Midland, Michigan.

The ratios of the 2-(thiocyanomethylthio)benzothiazole to 2,2-dibromo-3-nitrilopropionamide in the compositions of this invention are adjusted to provide a synergistic behavior to the composition. These synergistic weight ratios range from about 90:10 parts of 2-(thiocyanomethylthio)benzothiazole to 10:90 parts of 2,2-dibromo-3-nitrilopropionamide. When the microbicides are present in these ratios, the resulting composition possesses a higher degree of effectiveness against microorganisms than the individual microbicides comprising the mixture.

As to the amount of the compositions to be added to the various systems, suitable and preferred quantities vary according to the specific system in which the compositions are used. When added to aqueous systems to control slime-forming microorganisms, the suitable and preferred quantities vary from 0.01 to 5000 parts and 0.1 to 1000 parts, respectively, per million parts of water present in the system. It will be understood, of course, that larger quantities of the compositions may be used with no detrimental effect, but such larger quantities increase the cost of treatment with limited material benefit.

In order to disclose the nature of the invention still more clearly, the following illustrative examples will be given. It is understood, however, that the invention is not to be limited to the specific conditions or details set forth in these examples, except insofar as such limitations are specified in the appended claims.

EXAMPLE 1

In this example, synergism was demonstrated in separate experiments by testing 2-(thiocyanomethylthio)-benzothiazole, designated as Compound A, and 2,2-dibromo-3-nitrilopropionamide, designated as Compound B, in one series of tests in varying ratios and over a range of concentrations against the fungus *Chaetomium globosum*. The compounds and mixtures were tested by the pulp-substrate method described in U.S. Pat. No. 3,193,448, which disclosure is hereby made a part of this application. The lowest concentration of each compound or mixture which completely prevented growth of the fungus was taken as the end point. End points for the various mixtures were then compared with end points for the pure active ingredients alone in concommitantly prepared flasks. Synergism was demonstrated by the method described by Kull, F. C., Eisman, P. C., Sylwestrowicz, H. D., and Mayer, R. L., Applied Microbiology 9, 538–541 (1961) wherein $$\frac{Q_A}{Q_a} + \frac{Q_B}{Q_b} \text{ is less than 1}$$

$Q_a$ = Concentration of Compound A in parts per million, acting alone, which produced an end point $Q_b$ = Concentration of Compound B, in parts per million, acting alone, which produced an end point $Q_A$ = Concentration of Compound A, in parts per million, in the mixture, which produced an end point $Q_B$ = Concentration of Compound B, in parts per million, in the mixture, which produced an end point When the sum of $Q_A/Q_a$ and $Q_B/Q_b$ is greater than one, antagonism is indicated and when the sum is equal to one, additivity is indicated. When less than one, then it is synergistic.

This procedure for demonstrating the synergism of the compositions of this invention is a widely used and acceptable procedure. More detailed information is provided in the article by Kull et al. Further information concerning this procedure is contained in U.S. Pat. No. 3,231,509, which disclosure is hereby made a part of this application.

The results obtained in this Example are included in Table 1.

TABLE 1

Experiment 1
Test organism *Chaetomium globosum*

| Weight ratio of A to B | $Q_a$ | $Q_A$ | $Q_b$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| 100/0 | 2 | — | — | — | — | — | — | — |
| 90/10 | — | 1.8 | — | 0.2 | 2 | 0.9 | 0.006 | 0.91 |
| 70/30 | — | 1.4 | — | 0.6 | 2 | 0.7 | 0.02 | 0.72 |
| 30/70 | — | 0.6 | — | 1.4 | 2 | 0.3 | 0.04 | 0.34 |
| 10/90 | — | 0.4 | — | 3.6 | 4 | 0.2 | 0.11 | 0.31 |
| 0/100 | — | — | 32 | — | — | — | — | — |

In this table, the column at the extreme left describes the ratio of compound A to compound B. The designation, 100/0, means that compound A was tested with none of B present. $Q_a$ is the concentration of A in parts per million that completely inhibited the growth of *Chaetomium globosum*.

In the second line, the data show that two parts per million of the mixture inhibited growth. The ratio of A to B was 90/10, so the concentration of A in the mixture was 1.8 parts per million ($Q_A$) and the concentration of B was 0.2 part per million ($Q_B$). The bottom line shows that 32 parts per million ($Q_b$) of compound B was required to inhibit completely the *Chaetomium globosum* when it was tested without any A present.

As stated above, Kull, et al. then calculated $Q_A/Q_a$ which in this example is 0.9, and $Q_B/Q_b$ which is 0.006. The sum of these two ratios is 0.9+0.006=0.906 or 0.91, and since this value is less than one, synergism is indicated.

Table 1 further shows that the other mixtures of A and B also provided ratio sums of less than 1.

EXAMPLE 2

The effectiveness of compounds A and B described in Example 1, and of mixtures of A and B, was determined against *Enterobacter aerogenes* at pH 5.5 using the pulp-substrate method described in U.S. Pat. No. 2,881,070, which disclosure is hereby made a part of this application. The method described in Example 1 was then used to demonstrate that a synergistic effect was also obtained in controlling the test bacterium. The end point in these calculations was the concentration in parts per million required for 80 percent kill. The results of these tests are described in Table 2.

TABLE 2

Experiment 1
Test organism *Enterobacter aerogenes*

| Weight ratio of A to B | $Q_a$ | $Q_A$ | $Q_b$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| 100/0 | 30 | — | — | — | — | — | — | — |
| 30/70 | — | 0.3 | — | 0.7 | 1.0 | 0.01 | 0.7 | 0.71 |
| 10/90 | — | 0.1 | — | 0.9 | 1.0 | 0.003 | 0.9 | 0.9 |
| 0/100 | — | — | 1.0 | — | — | — | — | — |

EXAMPLE 3

The effectiveness of compounds A and B described in Example 1 and of mixtures A and B was determined against the alga *Chlorococcum hypnosporum* in Difco algae broth having the following composition:

| Compound | Ingredients per liter |
|---|---|
| Sodium nitrate | 1.0 gram |
| Ammonium chloride | 50.0 milligrams |
| Calcium chloride | 58.0 milligrams |
| Magnesium sulfate | 0.513 gram |
| Dipotassium phosphate | 0.25 gram |
| Ferric chloride | 3.0 grams |

Forty-gram portions of the algae medium were added to 250-milliliter Pyrex Erlenmeyer flasks fitted with loose metal caps and then sterilized. Each of the following substances were then added to the flasks in the order listed:

1. Sterile algae medium as required in each individual case to bring the total weight of the contents of each flask to 50 grams, after allowing for all subsequent additions specified hereinafter.
2. Solution of toxicant or control agent to be evaluated in each test to give the concentration desired in parts per million by weight.
3. *Chlorococcum hypnosporum* was the alga use for these tests. The inoculum was an amount sufficient to give excellent growth in the controls after 14 days. This was achieved by adding one milliliter of a 14-day-old culture having luxuriant growth. *Chlorococcum hypnosporum*, Starr No. 119, was obtained from the Culture Collection of Algae at Indiana University, Bloomington, Indiana.

After the inoculum of the test alga had been added, the flasks were allowed to incubate at a temperature of 28°±2° C. under fluorescent illumination of 250 foot-candle intensity (8 hours, 16 hours darkness) for a period adequate for growth in the controls (those portions of medium which contained no toxicant). Observations of growth were made after 28 days on the basis of the following key:

4 = Excellent
3 = Good
2 = Poor
1 = Very poor, scant, questionable
0 = No growth Synergism is apparent when *Chlorococcum hypnosporum* was the test organism. The method described in Example 1 was used to demonstrate that a synergistic effect was also obtained in controlling *Chlorococcum hypnosporum*.

TABLE 3

Experiment 1
Test organism *Chlorococcum hypnosporum*

| | Quantities producing end points | | | | | | | |
|---|---|---|---|---|---|---|---|---|
| Weight ratio of A to B | $Q_a$ | $Q_A$ | $Q_b$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
| | Parts per million | | | | | | | |
| 100/0 | 2 | — | — | — | — | — | — | — |
| 30/70 | — | 0.3 | — | 0.7 | 1 | 0.15 | 0.7 | 0.85 |
| 10/90 | — | 0.1 | — | 0.9 | 1 | 0.05 | 0.9 | 0.95 |
| 0/100 | — | — | 1.0 | — | — | — | — | — |

Among the microorganisms that are responsible for the growth of slime in pulp and paper mills are the bacterium *Enterobacter aerogenes* and the fungi *Aspergillus niger*, *Penicillium roqueforti*, and *Chaetomium globosom*. Algae are not ordinarily considered as major slime-forming organisms in pulp and paper mills, but algae do develop in the fresh water supplies in some instances. In cooling towers, algae are a major cause of fouling and reduced efficiency in addition to bacteria and fungi. It is thus apparent from the experimental data described in the foregoing Examples that the compositions of this invention will provide control of slime-forming microorganisms in aqueous systems.

The compositions of this invention may be used diluted with a carrier which may be liquid or solid. Dusts may be prepared with a finely divided solid such as talc, clay, pyrophyllite, diatomaceous earth, hydrated silica, calcium silicate, or magnesium carbonate. If desired, wetting and/or dispersing agents may be used. When the proportions of these are increased, there results a wettable powder, which may be dispersed in water and applied from a spray.

Dusts may contain one percent to 15 percent of the compounds of this invention, while wettable powders may contain up to 50 percent or more of one or more of these compounds.

A typical formulation of a wettable powder comprises 20 percent to 50 percent of the compositions of this invention, 45 percent to 75 percent of one or more finely divided solids, one percent to five percent of a wetting agent, and one percent to five percent of a dispersing agent. Typical wetting agents include sodium dodecyl sulfate, sodium nonylbenzene sulfonate, sodium dioctyl sulfosuccinate, octylphenoxypolyethoxyethanol, or other nonionic agents, such as ethylene and/or propylene oxide condensates with long chained alcohols, mercaptans, amines, or carboxylic acids. Typical dispersing agents include the sodium sulfonate of condensed naphthalene-formaldehyde and lignin sulfonates.

Liquid concentrates may also be used. These are prepared by taking up the compositions of this invention in an organic solvent together with one or more surface active agents.

The compounds of this invention may be used in conjunction with other microbicidal agents and also in conjunction with miticides or insecticides or other pesticides.

While particular embodiments of the invention have been described, it will be understood, of course, that the invention is not limited thereto since many modifications may be made, and it is, therefore, contemplates to cover by the appended claims any such modifications as fall within the true spirit and scope of the invention.

The invention having thus been described, what is claimed and desired to be secured by Letters Patent is:

1. A synergistic microbiocidal composition comprising 10 to 90 parts by weight of 2-(thiocyanomethylthio)-benzothiazole and 90 to 10 parts by weight of 2,2-dibromo-3-nitrilopropionamide.

2. A synergistic microbiocidal composition comprising 10 to 30 parts by weight of 2-(thiocyanomethylthio)-benzothiazole and 70 to 90 parts by weight of 2,2-dibromo-3-nitrilopropionamide.

3. The method of controlling the growth and deposition of slime-forming organisms in flowing-water systems which comprises adding to the flowing-water in such system a composition as defined in claim 1 in an amount between approximately 0.1 and approximately 1000 parts per million parts of the water.

4. The method of controlling the growth and deposition of algae in flowing-water systems which comprises adding to the flowing water in such system a composition as defined in claim 1 in an amount between approximately 0.1 and approximately 1000 parts per million parts of the water.

5. The method of controlling slime in pulp and paper mill systems which comprises adding to an aqeous suspension containing the pulp a composition as defined in claim 1 in an amount between approximately 0.1 and approximately 1000 parts per million parts of the water.

6. The method of controlling the growth and proliferation of sulfate-reducing bacteria as well as species of slime-forming microorganisms in secondary recovery petroleum operations, which comprises adding to the water in such systems a composition as defined in claim 1 in an amount between approximately 0.1 and approximately 1000 parts per million parts of the water.

7. The method of controlling the growth and proliferation of algae, bacteria, and fungi in fresh water which comprises adding to said fresh water the composition defined in claim 1 in an amount between approximately 0.1 and approximately 1000 parts per million parts of the water.

8. The method of controlling the growth and proliferation of algae, bacteria, and fungi in cooling water which comprises adding to said cooling water the composition defined in claim 1 in an amount between approximately 0.1 and approximately 1000 parts per million parts of the water.

* * * * *